US00PP09326P

United States Patent [19]

Zary

[11] Patent Number: Plant 9,326

[45] Date of Patent: Oct. 17, 1995

[54] HYBRID TEA ROSE PLANT NAMED 'JACLOGO'

[75] Inventor: Keith W. Zary, Thousand Oaks, Calif.

[73] Assignee: Bear Creek Gardens, Inc., Medford, Oreg.

[21] Appl. No.: 316,899

[22] Filed: Oct. 3, 1994

[51] Int. Cl.[6] ..... A01H 5/00

[52] U.S. Cl. ..... Plt./11

[58] Field of Search ..... Plt./11, 13, 15, Plt./16

[56] References Cited

U.S. PATENT DOCUMENTS

P.P. 6,317 10/1988 Warriner ..... Plt./11

*Primary Examiner*—Howard J. Locker

*Attorney, Agent, or Firm*—Klarquist Sparkman Campbell Leigh & Whinston

[57] ABSTRACT

A hybrid tea rose plant having novel flower color, vigorous upright growth, good production of flowers, resistance to mildew, and dark green, glossy foliage.

1 Drawing Sheet

The present invention relates to a new and distinct variety of rose plant of the hybrid tea class which was originated by me by crossing the variety KORenlo, U.S. Plant Pat. No. 5,679, with the variety JACgold, U.S. Plant Pat. No. 5,121.

The primary objective of this breeding was to produce a new rose variety having the productivity and long vase life of the female parent, combined with the dark green, glossy foliage, powdery mildew resistance and long stems of the male parent. The objective was substantially achieved, along with other desirable improvements, as evidenced by the following unique combination of characteristics that are outstanding in the new variety and that distinguish it from its parents, as well as from all other varieties of which I am aware:

1. Novel flower color;
2. Vigorous upright growth;
3. Good production of flowers;
4. Resistance to mildew; and
5. Dark green glossy foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—KORenlo.

*Pollen parent.*—JACgold.

Classification:

*Botanical.*—*Rosa hybrida.*

*Commercial.*—Hybrid tea.

FLOWER

Observations made from specimens grown in a greenhouse environment at Somis, Calif., from January to June 1994.

Blooming habit: Continuous.

Bud:

*Size*—1½ inches long when the petals start to unfurl.

*Form.*—The bud form is long, pointed avoid.

*Color.*—When sepals first divide, bud color is Yellow Group 13B. The petal margins (outer ¼ of the petal) are Orange Group 25B. When half blown, the upper sides of the petals are Yellow Group 13B and the petal margins are Orange Group 25B. The outer petals will change on the margins to Red Group 48C in full sunlight; and the lower sides of the petals are Yellow Group 13B with margins of Orange Group 25B.

*Sepals.*—Color: Yellow Green Group 146B. Surface texture: Covered in fine hairs. There are three normally appendaged sepals. There are two unappendaged sepals with hairy edges.

*Receptacle.*—Color: Green Group 143B. Shape: Funnel. Size: Medium (5/16 inch×¼ inch). Surface: Smooth.

*Peduncle.*—Length: Medium (3 inches). Surface: Smooth, glandular. Color: Medium green. Strength: Stiff, erect.

Bloom:

*Size.*—Medium. Average open size is 4 inches.

*Borne.*—Singly.

*Stems.*—Long, strong. Average length is about 22 inches to 26 inches.

*Form.*—When first open: High centered. Permanence: Retains its form to the end, outer petals curl back.

*Petalage.*—Number of petals under normal conditions: 35.

*Color.*—The upper side of the petals is Yellow Group 13B. The petal margins are Orange Group 25B. The reverse side of the petals is Yellow Group 13B. The petal margins are Orange Group 25B. The base of each petal is Yellow Group 13A. The major color on the upper side is Yellow Group 13B.

*Variegations.*—None.

*Discoloration.*—The general tonality at the end of the first day: Little change. At the end of the third day, as the flower opens, there is a gradual increase in Orange Group 25B as more of the petal is exposed to bright sunlight. By day five, some of the Orange Group 25B on the petal edges has changed to Red Group 48C.

*Fragrance.*—Slight.

Petals:

*Texture.*—Thick, leathery.

*Shape.*—Round.
*Form.*—Tips slightly recurved, edges slightly quilled.
*Arrangement.*—Imbricated, with a few petaloids in the center.
*Persistence.*—Drop off cleanly.
*Lastingness.*—On the plant: Long (7 to 8 days). As a cut flower: Long (9 to 10 days).

Reproductive parts:
*Anthers.*—Size: Medium. Quantity: Many. Color: Yellow. Arrangement: Regular around styles.
*Filaments.*—Color: Yellow.
*Pollen.*—Color: Gold yellow.
*Styles.*—Color: Red.
*Stigmas.*—Color: Greenish white.

Form: Bush.

Growth: Vigorous, upright, branching.

Foliage: Number of leaflets on normal mid-stem leaves: 5 or 7.
*Size.*—Large (7 inches×5 inches).
*Quantity.*—Normal.
*Color.*—New foliage: Greyed Red Group 178B. Old foliage: Green Group 139A on the upper side, and Green Group 137D on the lower side.

Leaflets:
*Shape.*—Pointed oval.
*Texture.*—Upper side: Leathery, glossy.
*Edge.*—Serrated.
*Serration.*—Single, small.
*Petiole rachis.*—Color: Reddish.
*Petiole underside.*—Smooth.
*Stipules.*—Medium (⅝ inch), serrated, bearded.
*Disease resistance.*—Resistant to mildew under normal greenhouse growing conditions at Somis, Calif.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Medium, hooked downward.
*Color when young.*—Red.

Small prickles:
*Quantity.*—On main stalks: None. On laterals: None.

I claim:

1. A new and distinct variety of rose plant of the hybrid tea class, substantially as herein shown and described, characterized particularly as to novelty by the unique combination of its novel flower color, vigorous upright growth, good production of flowers, resistance to mildew, and dark green, glossy foliage.

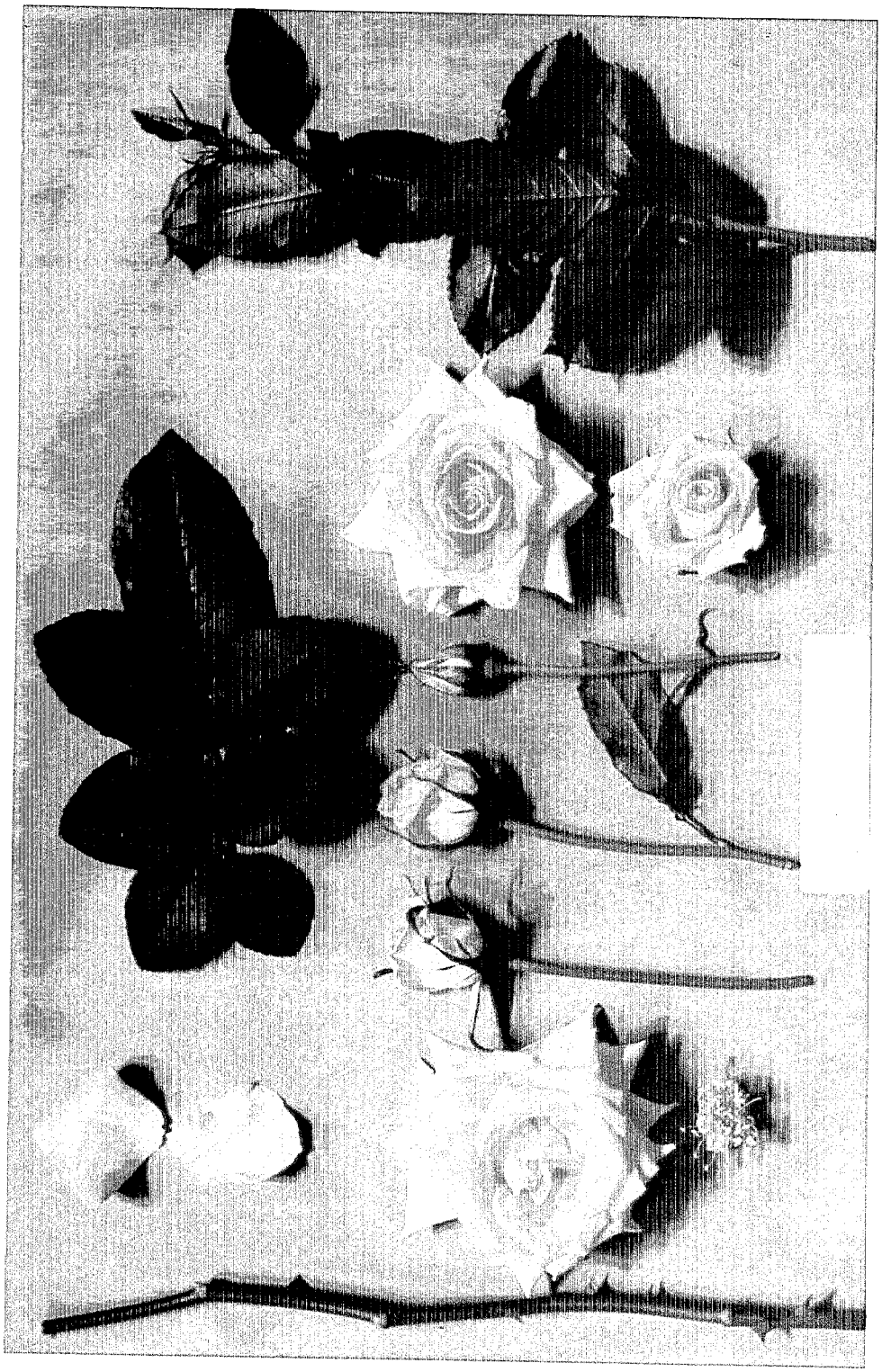

* * * * *